United States Patent [19]

Murray

[11] Patent Number: 4,847,301

[45] Date of Patent: Jul. 11, 1989

[54] METHODS OF USE OF α-(AMINOALKYL)-ARYLACETIC ACID DERIVATIVES

[75] Inventor: Robert J. Murray, Penfield, N.Y.

[73] Assignee: Pennwalt Corporation, Philadelphia, Pa.

[21] Appl. No.: 224,646

[22] Filed: Jul. 27, 1988

Related U.S. Application Data

[62] Division of Ser. No. 797,590, Nov. 13, 1985, Pat. No. 4,783,537.

[51] Int. Cl.$^4$ ............................................. A61K 31/445
[52] U.S. Cl. .................... 514/624; 514/212; 514/277; 514/417; 514/428; 514/459; 514/546; 514/567
[58] Field of Search ............... 514/620, 212, 277, 417, 514/428, 459, 567, 546

[56] References Cited

U.S. PATENT DOCUMENTS

| | | | |
|---|---|---|---|
| 2,776,282 | 1/1957 | Cusic | 260/247.2 |
| 2,854,472 | 9/1958 | Rorig | 564/165 |
| 3,078,275 | 2/1963 | Moffett et al. | 564/165 |
| 3,225,054 | 12/1965 | Cusic et al. | 546/330 |
| 4,225,606 | 9/1980 | Sanczuk et al. | 546/194 |
| 4,277,471 | 7/1981 | Lacefield et al. | 564/165 |
| 4,356,177 | 10/1982 | Demarne et al. | 546/194 |
| 4,539,316 | 9/1985 | Algieri et al. | 546/194 |
| 4,783,537 | 11/1988 | Murray | 546/187 |

FOREIGN PATENT DOCUMENTS

| | | |
|---|---|---|
| 617730 | 11/1962 | Belgium . |
| 2810143 | 9/1978 | Fed. Rep. of Germany ...... 514/620 |
| 2273532 | 1/1976 | France . |
| 666778 | 2/1952 | United Kingdom ................ 546/194 |
| 771814 | 4/1957 | United Kingdom . |

OTHER PUBLICATIONS

Chemical Abstract 84:105383q, vol. 84, pp. 558, 1976.
Chemical Abstract 51:8813e, 1957.
H. Tron Loisel et al., Eur. J. Med. Chem.–Chimica Therapeutica, Jul.–Aug. 1978, vol. 13 (4), pp. 351–356.
R. E. Stenseth, "The Preparation of 2-Ketopolymethyleneimines", Ph.D. Dissertation, University of Michigan, 1961.
Mathieu et al., Ind. Chim. Belge, vol. 32, 1967, pp. 234–238.
Kato et al., Yakugaku Zasshi, vol. 85 (9), 1965, pp. 812–816.
C. A. Bernhart et al., J. Med. Chem., vol. 26, 1983, pp. 451–455.

Primary Examiner—Richard L. Raymond
Assistant Examiner—Susan P. Treanor
Attorney, Agent, or Firm—Seidel, Gonda, Lavorgna & Monaco

[57] ABSTRACT

Novel α-aryl-α-(ω-aminoalkyl)-α-[hydroxy(aralkyl and cycloalkyl)]acetic acid derivatives and α-aryl-α-(ω-aminoalkyl)-α[alkanoyloxy(aralkyl and cycloalkyl)]acetic acid derivatives, such as N,N-dimethyl-2-(hydroxyphenylmethyl)-4-dimethylamino-2-phenylbutanamide, 2-(hydroxyphenylmethyl)-5-dimethylamino-2-phenylpentanenitrile, ethyl 2-(hydroxyphenylmethyl)-5-dimethylamino-2-phenylpentanoate, and N,N-dimethyl-2[(acetyloxy)phenylmethyl]-4-dimethylamino-2-phenylbutanamide, useful in the treatment of cardiovascular disease.

13 Claims, No Drawings

METHODS OF USE OF α-(AMINOALKYL)-ARYLACETIC ACID DERIVATIVES

This is a divisional of co-pending application Ser. No. 797,590 filed on Nov. 13, 1985, now U.S. Pat. No. 4,783,537.

BACKGROUND OF THE INVENTION

This invention pertains to novel α-aryl-α-(ω-aminoalkyl)-α-[hydroxy(aralkyl and cycloalkyl)]acetic acid derivatives and α-aryl-α-(ω-aminoalkyl)-α[alkanoyloxy(aralkyl and cycloalkyl)]acetic acid derivatives, useful in the treatment of cardiovascular disease.

Others have disclosed the synthesis of various α-aryl-α-(ω-aminoalkyl)-α-(aralkyl and cycloalkyl)acetic acid derivatives and one α-aryl-α-(ω-aminoalkyl)-[hydroxy(alkyl)]acetic acid derivative.

The synthesis of various α-(pyridyl)-α-(ω-aminoalkyl)-α-[aralkyl, cycloalkyl, alkyl and cycloalkyl(alkyl)]acetic acid derivatives, and measurements of their antiarrhythmic activities, were reported by C. A. Bernhart et al in "Synthesis and Antiarrhythmic Activity of New [(Dialkylamino)alkyl]pyridylacetamides", J. Med. Chem. 26, 451–455 (1983). In U.S. Pat. No. 4,356,177, the synthesis of α-(pyridyl)-α-(ω-aminoalkyl)-α-[cycloalkyl, alkyl, alkenyl, alkynyl, and cycloalkyl (alkyl)]acetic acid derivatives, and, in some instances, measurement of their antiarrhythmic activities were disclosed.

N,N-Dimethyl-4-dimethylamino-2-(1-hydroxypropyl)-2-phenylbutyramide, was described by R. E. Stenseth and Frederich F. Blicke in "Cyclization of Basic Amide Hydrochlorides, A New Synthesis of Substituted Lactams", The Journal of Organic Chemistry 34, 3007–3010 (1969). No biological data was reported.

In addition, various ω-amino-2-phenyl-2-pyridylbutyramides and ω-amino-2-phenyl-2-pyridylvaleramides, as eurhythmic agents, and the corresponding nitriles were reported in Chemical Abstracts (1963), Column 12522, (which cites Belgium Pat. No. 617,730 and two United States application dates). In U.S. Pat. No. 3,225,054, 4-dipropylamino-2-aryl-2-pyridylalkanamides, as eurhythmic, anti-inflammatory and diuretic agents, and the corresponding nitriles, were described. The synthesis of α-benzyl-α-[2-(dimethylamino)ethyl]-2-pyridine acetamide was described in Chemical Abstracts 63, 18019b, but no biological activity was discussed. Phenylacetic acid esters substituted on the α-carbon with alkyls, alkenes, alkynes, aralkyls, aryls, cycloalkyls, and cycloalkenyls, as well as with (dialkylamino)alkyl and cycloaminoalkyl groups were described in Chemical Abstracts 70, 55926g; some of these had antidepressant activity. British patent specification 771,814, "New Butyryl Amides and Processes for their Manufacture" disclosed disubstituted amides of α-phenyl-α-(2-pyridyl)-ω-(disubstituted-amino)-butyric acids as antihistaminic and antispasmodic agents.

BRIEF SUMMARY OF THE INVENTION

The compounds of the invention are those of formula (I):

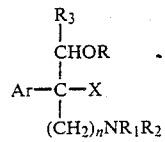

wherein
R is hydrogen or lower alkanoyl;
$R_1$ and $R_2$ are independently hydrogen, lower alkyl, or
lower cycloalkyl, or $R_1$ and $R_2$ together with their adjacent
nitrogen atom form a heterocyclic ring containing 4 to 6 carbon atoms;
$R_3$ is phenyl, substituted phenyl, 2-pyridyl, 3-pyridyl, 4-pyridyl, or lower cycloalkyl;
Ar is phenyl, substituted phenyl, or 2-pyridyl;
X is CN, $CO_2R_4$, or $CONR_5R_6$;
$R_4$ is hydrogen or lower alkyl;
$R_5$ and $R_6$ are independently hydrogen or lower alkyl, or
$R_5$ and $R_6$ together with their adjacent nitrogen atom form a heterocyclic ring containing 4 to 6 carbon atoms; and
n is 2 or 3, including all enantiomers thereof and mixtures of enantiomers thereof.

Preferred compounds of the invention are the compounds of the invention provided:
(1) $R_3$ is not 3-pyridyl or 4-pyridyl;
(2) $R_3$ is not 2-pyridyl in a compound in which X is $CONHCH_3$, R is H, Ar is phenyl, and n is 2;
(3) $R_3$ is not 2-pyridyl in a compound in which X is CN, R is H, Ar is phenyl, and n is 3; and
(4) $R_3$ is not phenyl substituted with lower alkoxy in a compound in which X is $CON(CH_3)_2$, R is H, Ar is phenyl, and n is 3.

In subgeneric aspects of the invention, the compounds of the invention and the preferred compounds are defined as above except that $R_3$ is not cycloalkyl.

The invention also encompasses processes for the preparation of the compounds of the invention.

The invention is also a method of treating angina comprising the administration, to a mammal in need of such treatment, of either a compound of the invention or a compound of formula I in which R, $R_1$, $R_2$, Ar, X, $R_4$, $R_5$, $R_6$ and n are defined as for the compounds of the invention and $R_3$ is lower alkyl, including all enantiomers thereof and mixtures of enantiomers thereof.

The invention is also a method of treating an antiarrhythmic condition comprising the administration, to a mammal in need of such treatment, of either a preferred compound of the invention or a compound of formula I in which R, $R_1$, $R_2$, Ar, X, $R_4$, $R_5$, $R_6$, and n are defined as for the compounds of the invention and $R_3$ is lower alkyl, including all enantiomers thereof and mixtures of enantiomers thereof.

DETAILED DESCRIPTION

The compounds of the invention are calcium antagonists and, as such, are useful in the treatment of angina in a mammal (e.g., humans). Furthermore, their calcium antagonist activity is likely to render the compounds of the invention useful in the treatment of hypertension and arrhythmia. It has also been suggested that such activity will render compounds useful in the treatment of asthma, migraine and artherosclerosis. The calcium antagonist activity of the compounds of the invention can be demonstrated using the calcium receptor binding assay of R. J. Gould et al, Proceedings of the National Academy of Sciences, USA, 79, 3656–3660 (1982) to show a reversal of verapamil inhibition of 3H-nitrendipine binding.

The preferred compounds of this invention have antiarrhythmic activity in addition to activity against angina. The antiarrhythmic activity of a preferred compound can be demonstrated by the reversal of ouabain-induced arrhythmias in an anesthetized dog that has been prepared for recording systemic arterial blood pressure and lead II ECG. After a 30 minute stabilization period, a priming dose of 50 μg/kg (iv) ouabain is given. At 15 minute intervals additional increments of 10 μg/kg ouabain is given until either ventricular tachycardia or multifocal ectopic arrhythmias are obtained. The test compound is then administered at 10 mg/kg (iv) or less and the ECG is monitored for changes indicative of reversal of the arrhythmias. A compound is considered active if it causes a return to normal heart action.

An appropriate procedure for administering either a compound of the invention to a mammal suffering from angina, or a preferred compound of the invention to a mammal suffering from arrhythmia, is at a dose of about 0.1 to 100 mg/kg of body weight per day as a single dose, but preferably divided among two to four daily doses, and preferably orally, although the subcutaneous, intramuscular, intravenous or intraperitoneal routes can also be employed. The dosage may be varied, depending upon the requirements of the patient, the severity of the condition being treated, and the compound being employed.

Compounds of formula I in which R, $R_1$, $R_2$, Ar, X, $R_4$, $R_5$, $R_6$, and n are defined as for the compounds of the invention and $R_3$ is lower alkyl, including all enantiomers thereof and mixtures of enantiomers thereof, have both calcium antagonist activity (and, as such, are useful in the treatment of angina) and antiarrhythmic activity. An appropriate means of administering these compounds to a mammal suffering from angina or arrhythmia is the same as that for administering a compound of the invention, or a preferred compound of the invention, to such a mammal.

Especially preferred compounds are those in which R is hydrogen or acetyl, $R_1$ and $R_2$ are either both $CH_3$, both isopropyl, or together with their adjacent N form piperidino; Ar is phenyl, and X is CN, $CO_2C_2H_5$, $CONHCH_3$, or $CON(CH_3)_2$. Of these, particularly preferred as anti-arrhythmics are N,N-dimethyl-2-(hydroxyphenylmethyl)-4-dimethylamino-2-phenylbutanamide, ethyl 2-[hydroxy(2-pyridyl)methyl]-4-dimethylamino-2-phenyl butanoate, N,N-dimethyl-2-(hydroxyphenylmethyl)-4-diisopropylamino-2-phenylbutanamide, N,N-dimethyl-2-(hydroxy phenylmethyl)-5-dimethylamino-2-phenylpentanamide, ethyl 2-(hydroxyphenylmethyl)-5-dimethylamino-2-phenylpentanoate, N,N-dimethyl-2-[hydroxy(4-methoxyphenyl)methyl]-4-dimethylamino-2-phenylbutanamide, N,N-dimethyl-2[(acetoxy)phenylmethyl]-4-dimethylamino-2-phenylbutanamide, N,N-dimethyl-2-[(acetyloxy)(4-methoxyphenyl)methyl]-4-dimethylamino-2-phenylbutanamide (also particularly preferred as a calcium antagonist), N,N-dimethyl-2-(hydroxyphenylmethyl-4-piperidino-2-phenyl butanamide, N,N-dimethyl-2-(hydroxyphenylmethyl)-5-diisopropylamino-2-phenylpentanamide, and N,N-dimethyl-2-(hydroxyphenylmethyl)-5-piperidino-2-phenylpentanamide.

Lower alkyl and lower alkoxy contain 1 to 4 carbon atoms. Lower alkanoyl contains two to four carbon atoms, including the carbon atom attached by a double bond to the alkanoyl moiety. Lower cycloalkyl groups contain 3 to 6 carbon atoms. A heterocyclic ring contains 4 to 6 carbon atoms, one or two nitrogen atoms, and either zero or one oxygen atoms; it is exemplified by pyrrolidine, piperidine, morpholine, piperazine, and 1H-hexahydroazepine. Substituted phenyl is phenyl that is either monosubstituted or disubstituted, and each substituent is selected from the group consisting of halogen (preferably chlorine or bromine), lower alkyl, lower alkoxy, amino, nitro, or hydroxy; substitution can occur at the ortho, meta, or para positions.

It will be recognized by those skilled in the art of organic chemistry that, because there are two assymetric carbon atoms in each compound, each compound of the invention can exist as either of two diastereoisomers (the threo diastereoisomers and the erythro diastereoisomer). Furthermore, each diastereoisomer has two enantiomeric forms, corresponding to its two optical enantiomers. Therefore, each compound of the invention can exist in any one of four enantiomeric forms.

Each claim to a compound includes its pharmaceutically acceptable acid addition salts. Acid addition salts include those derived from both organic and inorganic acids, such as, for example, acetic acid, maleic acid, fumaric acid, succinic acid, succinamic acid, tartaric acid, citric acid, lactic acid, hydrochloric acid, hydrobromic acid, hydroiodic acid, sulfuric acid, phosphoric acid, and the like.

PREPARATION OF COMPOUNDS

The methods for synthesizing the compounds of this invention are summarized in Charts A and B below. The encircled letters identify each method as either Method A, B, C, D, F or G, and "hyds" stands for hydrolysis. In chart A, $Z_1$ is a suitable nitrogen protecting group and $Z_2$ is either $R_2$ or together with $Z_1$ and the adjoining nitrogen forms a suitable nitrogen protecting group. Chart B illustrates the preferred methods for preparing the compounds described in that chart.

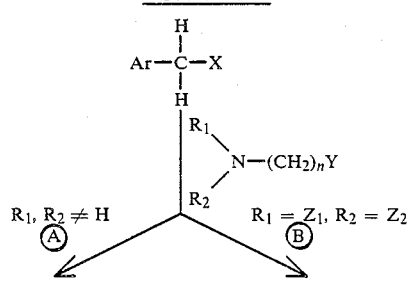

CHART A

-continued
CHART A

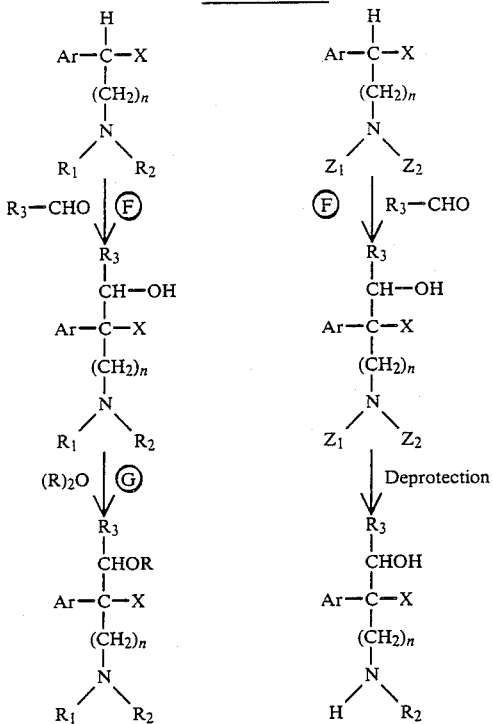

CHART B

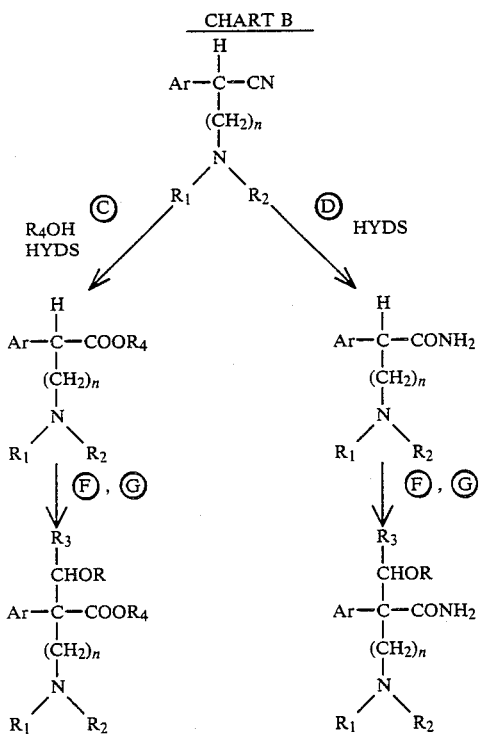

ABBREVIATIONS

For the sake of brevity, n-BuLi means n-butyl lithium, LDA means lithium diisopropylamide, THF means tetrahydrofuran, MeOH means methanol, EtOH means ethanol, EtOAc means ethyl acetate, $Et_2O$ means ethyl ether, RT means room temperature (about 23° C.), aq means aqueous, hr means hour(s), min means minute(s), mp means melting point, and bp means boiling point.

Temperatures are in degrees centigrade.

In discussions of chromatographic procedures, $r_f$ refers to the ratio $D_1:D_2$ where $D_1$ and $D_2$ are the average distances traveled along the chromatographic plate by the diastereoisomer and the solvent front, respectively, during the chromatographic process. The chromatographic procedure separates compounds into two diastereoisomers as one has a higher $r_f$ value (the high $r_f$ diastereoisomer) than the other (the low $r_f$ diastereoisomer). The terms "high melting point diastereoisomer" and "low melting point diastereoisomer" of a given compound refer to the diastereoisomers with the higher and lower melting points, respectively.

METHOD A

In the case where $R_1$ and $R_2$ are other than hydrogen, derivatives of the formula (II)

(wherein Ar, and X, and n, are as defined for the compounds of the invention) are available from the reaction of the corresponding alkanoic acid derivative $ArCH_2X$ (where Ar and X are as earlier defined) with a haloalkylamine $Y(CH_2)_nNR_1R_2$ (where $R_1$ and $R_2$ are independently lower alkyl or lower cycloalkyl, or where $R_1$ and $R_2$ together with their adjacent nitrogen atom form a heterocyclic ring containing 4 to 6 carbon atoms, and where n is 2 or 3, and Y is halo), in the presence of a strong base such as sodium amide ($NaNH_2$) and an inert solvent, at temperatures of about 70° to 140° C. depending on the solvent used.

METHOD B

Where either $R_1$ or both $R_1$ and $R_2$ are hydrogen, $ArCH_2X$ is reacted with either $Y(CH_2)_nNR_1Z_1$ or $Y(CH_2)_nNZ_1Z_2$, (wherein $Z_1$ is a suitable nitrogen protecting group, and $Z_2$ is either $R_2$ or together with $Z_1$ and the adjoining N group forms a protecting group such as pthalimido, n is 2 or 3, and Y is halo). The resulting adduct is reacted with the aldehyde, $R_3CHO$, to give the nitrogen-protected 2-(arylhydroxymethyl) derivatives, and the nitrogen-protecting groups are then removed by well-known methods to give the corresponding formula I compound where R is hydrogen and either $R_1$ or both $R_1$ and $R_2$ are hydrogen. Examples of suitable nitrogen-protecting groups are phthalimido, ethoxycarbonyl, benzyloxycarbonyl, and benzyl.

METHOD C

The formula II compounds where X is $CO_2R_4$ are prepared from the formula II compounds, where X is CN by reacting the nitrile with an alcohol ($R_4OH$) saturated with hydrogen chloride to form the iminoether hydrochloride (at about 20° to 100° C. depending on the alcohol), which is then hydrolyzed with water at about 15°–40° C. and basified to give the corresponding ester.

METHOD D

The intermediate formula II compounds where X is $CONH_2$ can be prepared by acid hydrolysis of the corresponding formula II compound where X is CN according to Bernhart et al. [For example, with sulfuric acid at about 80° to 100° C.].

METHOD E

Formation of the formula II compounds where X is $CONR_5R_6$, and $R_5$ or $R_6$ is lower alkyl, or $R_5$ and $R_6$ are both lower alkyl, are prepared by the procedures of Bernhardt et al and Stenseth et al. Formula II compounds where $R_5$ and $R_6$ together with their adjacent nitrogen atoms form a heterocyclic ring containing 4 to 6 carbon atoms are prepared according to Bernhardt et al and Stenseth et al.

METHOD F

The compounds of formula I wherein R is H can be conveniently prepared by contacting a compound of formula II (wherein Ar, X, n, $R_1$ and $R_2$ are as defined for the compounds of the invention) with an aldehyde $R_3CHO$ (wherein $R_3$ is as defined for the compounds of the invention) under nitrogen, in the presence of a strong base such as n-BuLi or LDA and an inert solvent such as THF or ether, at a temperature of from about $-70°$ to $+20°$ C., preferably at about 0° C.; and (b) recovering from the resultant reaction mixture the corresponding formula I compound.

METHOD G

Compounds of formula I in which R is H can in turn be conveniently converted to formula I compounds wherein R is lower alkanoyl by contacting the compound recovered in step (b) of Method F with an anhydride $(R)_2O$ (wherein R is lower alkanoyl) under nitrogen, in a solvent such pyridine, at ambient temperature and recovering from the resultant reaction mixture the desired compound.

SINGLE POT PROCEDURE (METHOD A PLUS METHOD F)

Starting with the $ArCH_2X$ derivative, the formula I compounds wherein R is hydrogen and neither $R_1$ nor $R_2$ are hydrogen can also be prepared in a single pot procedure by a sequential reaction, at about $-70°$ to $+20°$ C., in which said derivative is first reacted with about one equivalent of a strong base such as n-BuLi or LDA (about two equivalents of a strong base in the case where X is $CONHR_5$) and about one equivalent of the haloalkylamine $Y(CH_2)_nNR_1R_2$ (where $R_1$ and $R_2$ are alkyl or cycloalkyl, or $R_1$ and $R_2$ together with their adjacent nitrogen atom form a heterocyclic ring containing 4 to 6 carbon atoms, and where n is 2 or 3, and Y is halogen, preferably chlorine), and then reacted with about one additional equivalent of strong base such as n-BuLi or LDA and about one equivalent of the aldehyde $R_3CHO$ (where $R_3$ is as earlier defined). [For further details of this reaction, see Example 2.]

CHROMATOGRAPHY

Silica gel chromatography can be used to purify one diastereoisomer of a compound so that it is substantially free of the other. The elution solvent is a mixture of chloroform and methanol in which the methanol has been saturated with ammonia. The usual preferred ratio of chloroform to methanol is 95 to 5 (on a volume basis) but in some cases, alteration in the ratio may improve the chromatographic separation of the diastereoisomers. Where separation is poor, good separation can be achieved by increasing the ratio of silica to compound.

Silica gel chromatography is also useful to separate the compound, as a mixture of diastereoisomers, from impurities.

In the illustrations and Examples below, chromatography was done by silica gel chromatography using a ratio of chloroform to methanol of 95 to 5.

PREPARATION OF PURE DIASTEREOISOMERS AND PURE ENANTIOMERS

Method F is capable of generating each compound of the invention as a mixture of its two diastereomeric forms. A compound of the invention (when R is H) that exists as a mixture of its two diastereomeric forms may be further purified by silica gel chromatography so that each diastereoisomer exists essentially free of the other diastereoisomer. Purified diastereoisomers of compounds of the invention in which R is lower alkanoyl can be made according to Method G from the corresponding diastereoisomer in which R is H.

Each purified diastereoisomer will be a racemic mixture of two enantiomeric forms. Each purified diastereoisomeric form can be further purified by conventional methods for separating racemic mixtures into its components, so that each of its two enantiomeric components exists essentially free of the other. An example of such a method is the reaction of the racemic mixture with a stoichiometric amount of an optically active acid, such as $(+)$- or $(-)$- tartaric acid, $(+)$- or $(-)$-dibenzoyl tartaric acid, $(+)$- or $(-)$-monomethyl tartrate, or other derivative of tartaric acid. The reaction is carried out in a solvent in which the resulting salt of one of the enantiomers of the formula I compound has a different solubility than the resulting salt of the other enantiomer. Methanol, ethanol, or mixtures thereof, are preferred solvents. The preferentially insoluble enantiomer salt is then recovered and converted to the free base by conventional means. If the preferetcially insoluble enantiomer salt is still contaminated by an undesirably large amount of the other enantiomer salt, the reaction with tartaric acid or its derivative and the subsequent recovery and conversion steps may be repeated.

PHARMACEUTICAL PREPARATIONS

The compounds of this invention can be employed in the form of pharmaceutical preparations which contain the compound in association with a compatible pharmaceutical carrier. The compounds are thus presented in a form suitable for oral, parenteral or rectal administration, preferably oral. The dosage form may be a solution, suspension, tablet, capsule, or other suitable formulation.

ILLUSTRATIONS OF INTERMEDIATE PREPARATION

Illustration 1

Preparation of 4-Dimethylamino-2-phenylbutanenitrile

To a refluxing suspension of 35 g (0.90 mol) of $NaNH_2$ in 750 ml of toluene was added, dropwise with mechanical stirring under $N_2$, 100 g (0.85 mol) of phenylacetonitrile in 100 ml of toluene. The resulting suspension was stirred at reflux for a further 3 hr. Then, 92.5 g (0.86 mol) of 2-dimethylaminoethyl chloride in 50 ml of toluene was added dropwise, and the resulting dark suspension was first heated at reflux for 4½ hr and then stirred at RT for 16 hr. Water (1.5 liters) was added to the mixture, and the organic layer was separated and extracted with 1N HCl. The acid extract was cooled in ice and then basified with 2.5N NaOH. The product was extracted from the basified solution with Et$_2$O. The ethereal extract was dried (Na$_2$SO$_4$) and concentrated by evaporation. Distillation of the resulting crude oil afforded 35 g (52.5%) of the desired 4-dimethylamino-2-phenylbutanenitrile as a colorless oil; bp 95°–98°/0.1 mm.

Illustration 2

Preparation of
5-Dimethylamino-2-phenylpentanenitrile

Substitution of an equivalent quantity of 3-(dimethylamino)propyl chloride for 2-(dimethylamino)ethyl chloride in the procedure in Illustration 1 afforded the title compound as a colorless oil, bp 100°–102°/0.1 mm.

Illustration 3

Preparation of Ethyl
4-Dimethylamino-2-phenylbutanoate 10 gms of 4-dimethylamino-2-phenylbutanenitrile dissolved in 200 ml of EtOH saturated with HCl was heated at reflux for 4 hr while bubbling in HCl. The mixture was stirred at RT for 16 hrs and then the solvent was evaporated. The residual oil was dissolved in H$_2$O, neutralized with NaHCO$_3$ and extracted with Et$_2$O. The ethereal extracts were combined, dried (Na$_2$SO$_4$), concentrated and distilled to afford 10 gm (80.0%) of ethyl 4-dimethylamino-2-phenylbutanoate as a colorless oil, bp 101°–105°/0.2 mm.

Illustration 4

Preparation of Ethyl
5-Dimethylamino-2-phenylpentanoate

Treatment of 5-dimethylamino-2-phenylpentanenitrile in a fashion similar to the treatment of 4-dimethylamino-2-phenylbutanenitrile in the procedure in Illustration 3 afforded the title compound as a colorless oil, bp 107°–112°/0.2 mm.

Illustration 5

Preparation of
N-Methyl-4-dimethylamino-2-phenylbutanamide

To 7.46 g (0.05 mol) of N-methyl phenylacetamide (prepared by reaction of phenylacetyl chloride with monomethylamine in CH$_2$Cl$_2$ solvent) dissolved in 70 ml of THF and cooled in an ice-bath to 0°, was added dropwise with stirring under N$_2$, 40 ml (0.10 mol) of a 2.5M solution of N-BuLi in n-hexane. After stirring at 0° for 30 min, the solution was treated by the rapid addition of 5.4 g (0.05 mol) of 2-(dimethylamino)ethyl chloride in 30 ml of THF and then stirred at 0° for 30 min. The reaction mixture was then poured into 250 ml of 1N HCl, ether was added and the aqueous layer was separated, basified with 2.5N NaOH and extracted with Et$_2$O. The ether extract was dried (Na$_2$SO$_4$), concentrated, and kugelrohr distilled to afford 9.2 g (83.5%) of N-methyl-4-dimethylamino-2-phenylbutanamide as a viscous. colorless oil; bp 130°–135°/0.1 mm.

Following essentially the procedure of Illustration 5 and replacing monomethylamine with
ethylamine,
propylamine, and
isopropylamine,
the following compounds can be made:
N-ethyl-4-dimethylamino-2-phenylbutanamide,
N-propyl-4-dimethylamino-2-phenylbutanamide, and
N-isopropyl-4-dimethylamino-2-phenylbutanamide.

Illustration 6

Preparation of
N-Methyl-5-dimethylamino-2-phenylpentanamide

Substitution of an equivalent quantity of 3-(dimethylamino)-propyl chloride for 2-(dimethylamino)ethyl chloride in the procedure in Illustration 5 afforded the title compound as a colorless oil, bp 145°–147°/0.1 mm.

Illustration 7

Preparation of
N,N-Dimethyl-4-dimethylamino-2-phenylbutanamide

To a mechanically-stirred, refluxing suspension of 5.85 g (0.15 mol) of NaNH$_2$ in 150 ml of toluene, was added dropwise under N$_2$, 50 ml of a toluene solution consisting of 16.3 g (0.1 mol) of N,N-dimethylphenylacetamide (prepared by reaction of phenylacetyl chloride and N,N-dimethylamine in CH$_2$Cl$_2$ solvent) in toluene, and the mixture was stirred at reflux for 4 hr. Then, 16.5g (0.15 mol) of 2-(dimethylamino)ethyl chloride in 100 ml of toluene was added dropwise. The mixture was refluxed for 6 hr and then stirred at RT for 16 hr. Water (150 ml) was added to the mixture, and then the organic layer was separated and extracted with 1N HCl. The acid extract was basified in the cold with 2.5N NaOH and the basic solution extracted with Et$_2$O. The ether extract was dried (Na$_2$SO$_4$), concentrated, and distilled to afford 18 g (76.8%) of N,N-dimethyl-4-dimethylamino-2-phenylbutanamide as a colorless oil, bp 108°–110°/0.2 mm.

Following essentially the same procedure of Illustration 7 and replacing phenylacetyl chloride with
4-chlorophenylacetyl chloride,
2-methylphenylacetyl chloride,
4-methoxyphenylacetyl chloride, and
3-nitrophenylacetyl chloride, the following compounds can be made:
N,N-Dimethyl-4-dimethylamino-2-(4-chlorophenyl)-butanamide,
N,N-Dimethyl-4-dimethylamino-2-(2-methylphenyl)-butanamide,
N,N-Dimethyl-4-dimethylamino-2-(4-methoxyphenyl)-butanamide, and
N,N-Dimethyl-4-dimethylamino-2-(3-nitrophenyl)-butanamide.

Following essentially the procedure of Illustration 7 and replacing N.N-dimethylamine by
N,N-diethylamine,
pyrrolidine,
piperidine, and
morpholine, the following compounds can be made:
N,N-Diethyl-4-dimethylamino-2-phenylbutanamide,
1-[(4-Dimethylamino-1-oxo-2-phenyl)butyl]pyrrolidine,
1-[(4-Dimethylamino-1-oxo-2-phenyl)butyl]piperidine, and
1-[(4-Dimethylamino-1-oxo-2-phenyl)butyl]morpholine.

Following essentially the same procedure, and replacing 2-(dimethylamino)ethyl chloride with the N-protected amino alkyl halides,
2-(N-benzyloxycarbonyl-N-methylamino)ethyl chloride,
2-(N-benzyl-N-ethylamino)ethyl chloride, and
2-phthalimidoethyl chloride;

the following compounds can be made:
N,N-dimethyl-4-[N-(benzyloxycarbonyl)-N-methylamino]-2-phenylbutanamide,
N,N-dimethyl-4-[N-benzyl-N-ethylamino]-2-phenylbutanamide, and
N,N-dimethyl-4-phthalimido-2-phenylbutanamide, respectively.

Illustration 8

Preparation of
N,N-Dimethyl-5-dimethylamino-2-phenylpentanamide

Substitution of one equivalent quantity of 3-(dimethylamino)propyl chloride for 2-(dimethylamino)ethyl chloride in the procedure in Illustration 7 afforded the title compound as a colorless oil, bp 150°–155°/2.0 mm.

Illustration 9

Preparation of
N,N-Dimethyl-4-diisopropylamino-2-phenylbutanamide

Substitution of one equivalent quantity of 2-(diisopropylamino)ethyl chloride for 2-(dimethylamino)ethyl chloride in the procedure in Illustration 7 afforded the title compound as a colorless oil, bp 140°–145°/0.1 mm.

Illustration 10

Preparation of
N,N-Dimethyl-5-diisopropylamino-2-phenylpentamid

Substitution of one equivalent quantity of 3-(diisopropylamino)propyl chloride for 2-(dimethylamino)ethyl chloride in the procedure in Illustration 7 afforded the title compound as a colorless oil, bp 138°–145°/0.1 mm.

Illustration 11

Preparation of
N,N-Dimethyl-4-piperidino-2-phenylbutanamide

Substitution of one equivalent quantity of 2-piperidinoethyl chloride for 2-(dimethylamino)ethyl chloride in the procedure in Illustration 7 afforded by the title compound as a colorless oil, bp 135°–138°/0.1 mm.

Illustration 12

Preparation of
N,N-Dimethyl-5-piperidino-2-phenylpentanamide

Substitution of one equivalent quantity of 3-piperidinopropyl chloride for 2-(dimethylamino)ethyl chloride in the procedure in Illustration 7 afforded by the title compound as a colorless oil, bp 140°–145°/0.1 mm.

Illustration 13

Preparation of N,N-Dimethyl-(2-pyridyl)acetamide

To 5.0 g of ethyl 2-pyridylacetate dissolved in 25 ml of MeOH was added 20 ml of dimethyl amine. The mixture was heated at 90° in a steel autoclave for 96 hrs. The solvent/amine mixture was allowed to evaporate until a residual oil was obtained. The residual oill was distilled to afford 4.5 g of the desired N,N-dimethyl-(2-pyridyl)acetamide as a free-flowing yellow oil, bp 105°–110°/0.5 mm.

Illustration 14

Preparation of
N,N-Dimethyl-4-dimethylamino-2-(2-pyridyl)butanami

Substitution of one equivalent quantity of N,N-dimethyl-(2-pyridyl)acetamide for N,N-dimethylphenylacetamide in the procedure in Illustration 7 afforded the title compound, bp 160°–165°/0.1 mm.

EXAMPLES OF THE PREPARATION OF FORMULA I COMPOUNDS

EXAMPLE 1

Preparation of
N,N-Dimethyl-2-(hydroxyphenylmethyl)-4-dimethylamino-2-phenylbutanamide To a solution of 11.7 g of LDA [prepared from 11.1 g (0.11 mol) of diisopropylamine and 44 ml (0.11 mol) of n-BuLi (2.5M in n-hexane)] in 200 ml of THF, was added at 0° under $N_2$, 100 ml of a solution of 23.2 g (0.10 mol) of N,N-dimethyl-4-dimethylamino-2-phenylbutanamide in 100 ml of THF, and the resulting solution was stirred at 0° for 30 min. Benzaldehyde (11.7 g, 0.11 mol) in 50 ml of THF was added dropwise over a period of 5 minutes and then the solution was stirred for 5 minutes at 0°. The mixture was poured into 1 liter of ice-cold 1N HCl yielding a colorless solution which was washed with $Et_2O$ to remove unreacted benzaldehyde, basified by adding 2.5N NaOH while stirring in the cold, and extracted with $Et_2O$. The ethereal extract was dried ($Na_2SO_4$) and evaporated to afford 30 gm of a yellow oil. Chromatography of the oil afforded 12.0 g of the high $r_f$ diastereoisomer of N,N-dimethyl-2-(hydroxyphenylmethyl)-4-dimethylamino-2-phenylbutanamide, plus 6.0 g of the low $r_f$ diastereoisomer.

Dissolution of the high $r_f$ diastereoisomer in EtOH, acidification with EtOH/HCl followed by dilution with $Et_2O$ gave the hydrochloride salt of the high $r_f$ diastereoisomer as a colorless powder, mp 210°–211°. [Anal. Calc'd. for $C_{21}H_{28}N_2O_2 \cdot HCl$: C, 66.74; H, 8.00; N, 7.41; Cl, 9.38. Found: C, 66.80; H, 7.99; N, 7.33; Cl, 9.78.]

Treatment of the low $r_f$ diastereoisomer in the same manner afforded its hydrochloride salt as a colorless solid, mp 203°–204°. [Anal. Calc'd for $C_{21}H_{28}N_2O_2 \cdot HCl$: C, 66.74; H, 8.00; N, 7.41; Cl, 9.38. Found: C, 66.87; H, 7.91; N, 7.39; Cl, 9.43.]

Following essentially the same procedure, and replacing N,N-dimethyl-4-dimethylamino-2-phenylbutanamide with
N,N-diethyl-4-dimethylamino-2-phenylbutanamide,
1-[(4-dimethylamino-1-oxo-2-phenyl)butyl]pyrrolidine,
1-[(4-dimethylamino-1-oxo-2-phenyl)butyl]piperidine, and
1-[(4-dimethylamino-1-oxo-2-phenyl)butyl]morpholine, the following compounds can be made:
N,N-diethyl-2-(hydroxyphenylmethyl)-4-dimethylamino-2-phenylbutanamide,
1-[[(2-(hydroxyphenylmethyl)-4-dimethylamino-1-oxo-2-phenyl]butyl]pyrrolidine,
1-[[2-(hydroxyphenylmethyl)-4-dimethylamino-1-oxo-2-phenyl]butyl]piperidine, and
1-[[2-(hydroxyphenylmethyl)-4-dimethylamino-1-oxo-2-phenyl]butyl]morpholine, respectively.

Following essentially the same procedure, and replacing N,N-dimethyl-4-dimethylamino-2-phenylbutanamide with the (N-protected aminoalkyl) amides, N,N-dimethyl-4-[N-benzyloxycarbonyl-N-methylamino]-2-phenyl-butanamide,
N,N-dimethyl-4-[N-benzyl-N-ethylamino]-2-phenyl-butanamide and
N,N-dimethyl-4-phthalimido-2-phenylbutanamide,
the following N-protected compounds can be made:
N,N-dimethyl-2-(hydroxyphenylmethyl)-4-(N-benzyloxycarbonyl-N-methylamino)-12-phenylbutanamide,
N,N-dimethyl-2-(hydroxyphenylmethyl)-4-(N-benzyl-N-ethylamino)-2-phenylbutanamide, and
N,N-dimethyl-2-(hydroxyphenylmethyl)-4-phthalimido-2-phenylbutanamide, respectively, and by using well-known techniques, e.g., hydrogenolysis and hydrazinolysis, the protecting groups are removed to give the following compounds:
N,N-dimethyl-2-(hydroxyphenylmethyl)-4-methylamino-2-phenybutanamide,
N,N-dimethyl-2-(hydroxyphenylmethyl)-4-ethylamino-2-phenylbutanamide, and
N,N-dimethyl-2-(hydroxyphenylmethyl)-4-amino-2-phenylbutanamide, respectively.

EXAMPLE 2

Preparation of
N-Methyl-2-(hydroxyphenylmethyl)-4-dimethylamino-2-phenylbutanamide To a solution of 7.46 g (0.05 mol) of N-methylphenylacetamide in 70 ml of THF, cooled in an ice-bath to 0°, was added dropwise with stirring under $N_2$, 40 ml of a 2.5M solution of n-BuLi in n-hexane. The solution was stirred at 0° for 30 min. Then, 5.4 g (0.05 mol) of 2(dimethylamino)ethyl chloride in 30 ml of THF were added to the solution. The resulting mixture was stirred at 0° for a further 2 hrs. The resulting clear solution was treated with an additional equivalent of n-BuLi (20 ml of 2.5M n-BuLi in n-hexane) and then stirred at 0° for 30 min. A total of 5.3 g (0.05 mol) of benzaldehyde in 20 ml of THF was added to the solution over a 5 min period. The resulting pale, yellow solution was stirred at 0° for an additional 5 min and then poured into 250 ml of ice-cold 1N HCl. The resulting colorless solution was washed with $Et_2O$, basified with 2.5N NaOH while stirring in the cold, and extracted with $CHCl_3$. The $CHCl_3$ extract was dried ($Na_2SO_4$) and evaporated to yield 15 g of a yellow oil. Chromatography of the oil afforded 4.5 g of N-methyl-2-(hydroxyphenylmethyl)-4-dimethylamino-2-phenylbutanamide as a mixture of diastereoisomers, mp 107°–115°. [Anal. Calc'd for $C_{20}H_{26}N_2O_2$: C, 73.59; H, 8.03; N, 8.58. Found: C, 73.71; H, 8.13; N, 8.47.]

EXAMPLE 3

Preparation of
N-Methyl-2[hydroxy(2-pyridyl)methyl]-4-dimethylamino-2-phenylbutanamide To 5.0 g (0.023 mol) of N-methyl-4-dimethylamino-2-phenylbutanamide dissolved in 70 ml of THF, was added with ice-cooling under $N_2$, 18.1 ml of a 2.5M solution of n-BuLi in n-hexane, and the resulting solution was stirred at 0° for 30 min. 2-Pyridinecarboxaldehyde (2.42 g, 0.023 mol) dissolved in 20 ml THF was added over a period of 5 min and, after stirring an additional 5 min, the reaction mixture was poured into 150 ml of ice-cold 1N HCl. The resulting clear solution was washed with $Et_2O$, basified with 2.5N NaOH while stirring in the cold, and extracted with $CHCl_3$. The $CHCl_3$ extract was dried ($Na_2SO_4$), and evaporated to afford 4.5 g of a yellow oil. Chromatography of the oil afforded 1.5 g of N-methyl-2-[hydroxy(2-pyridyl)methyl]-4-dimethylamino-2-phenylbutanamide as a mixture of diastereoisomers. [Anal. Calc'd for $C_{19}H_{25}N_3O_2$: C, 69.70; H, 7.70; N, 12.83. Found: C, 69.59; H, 7.73; N, 12.79.]

Following essentially the procedure of Example 3 and replacing N-methyl-4-dimethylamino-2-phenylbutanamide with
N-ethyl-4-dimethylamino-2-phenylbutanamide,
N-propyl-4-dimethylamino-2-phenylbutanamide, and
N-isopropyl-4-dimethylamino-2-phenylbutanamide,
the following compounds can be made:
N-ethyl-2-[hydroxy(2-pyridyl)methyl]-4-dimethylamino-2-phenylbutanamide,
N-propyl-2-[hydroxy(2-pyridyl)methyl]-4-dimethylamino-2-phenylbutanamide,
N-isopropyl-2-[hydroxy(2-pyridyl)methyl]-4-dimethylamino-2-phenylbutanamide.

EXAMPLE 4

Preparation of
2-[Hydroxy(2-pyridyl)methyl]-4-dimethylamino-2-phenylbutanenitrile To 9.4 g (0.05 mol) of 4-dimethylamino-2-phenylbutanenitrile dissolved in 100 ml of THF and cooled in an ice bath at 0°, was added dropwise with stirring under $N_2$, 20 ml of a 2.5M solution of n-buLi in n-hexane. After stirring at 0° for 30 min, 5.38 g (0.05 mol) of 2-pyridinecarboxaldehyde in 20 ml THF was added over a period of 5 min and the resulting mixture was stirred for 5 min at 0°. The reaction mixture was then poured into 250 ml of ice-cold 1N HCl and the resulting clear solution was washed with $Et_2O$. The ethereal extract was dried ($Na_2SO_4$) and evaporated to afford 10 gms of a dark oil. Crystallization of the oil from EtOAc/hexane yielded 6.2 g of 2-[hydroxy(2-pyridyl)methyl]-4-dimethylamino-2-phenylbutanenitrile as a mixture of a diastereoisomers. [Anal. Calc'd for $C_{18}H_{21}N_3O$: C, 73.18; H, 7.17; N, 14.23. Found: C, 72.93; H, 6.86; N, 14.18.]

EXAMPLE 5

Preparation of Ethyl
2-[Hydroxy(2-pyridyl)methyl]-4-dimethylamino-2-phenylbutanoate To a solution of 3.0 g of LDA [prepared from 2.85 g (0.028 mol) of diisopropylamine and 11.25 ml of a 2.5M solution of n-BuLi in n-hexane] in 50 ml of THF, was added at 0° under $N_2$, 5.9 g (0.026 mol) of ethyl 4-dimethylamino-2-phenylbutanoate dissolved in 20 ml of THF, and the resulting solution was stirred at 0° for 30 min. 2-Pyridinecarboxaldehyde (2.7 g, 0.026 mol) dissolved in 10 ml of THF was then added over a period of 5 min and the resulting mixture was stirred at 0° to 5 min. The reaction mixture was then poured into 150 ml of ice-cold 1N HCl and the resulting clear solution was washed with $Et_2O$, basified with 2.5N NaOH while stirring in the cold, and extracted with $Et_2O$. The ethereal extract was dried ($Na_2SO_4$) and evaporated to afford 7.2 g of a yellow oil. Chromatography, yielded 2.5 g of the high $r_f$ diastereoisomer of ethyl 2-[hydroxy-(2-pyridyl)methyl]-4-dimethylamino-2-phenylbutanoate as an oil and 4.0 g of the corresponding low $r_f$ diastereoisomer, also as an oil.

Dissolution of the high $r_f$ diastereoisomer in EtOH, acidification with EtOH/HCl followed by Et$_2$O gave the hydrochloride salt of the high $r_f$ diastereoisomer as a colorless solid, mp 188°–190°. [Anal. Calc'd for C$_{20}$H$_{26}$N$_2$O$_3$.2HCl: C, 57.83; H, 6.79; N, 6.74; Cl, 17.07. Found: C, 57.81; H, 7.06; N, 6.74; Cl, 17.02.]

Treatment of the low $r_f$ diastereoisomer in similar fashion yielded its hydrochloride salt as a colorless solid, mp 205°–207°. [Anal. Calc'd for C$_{20}$H$_{26}$N$_2$O$_3$.2HCl: C, 57.83; H, 6.79; N, 6.74; Cl, 17.07 Found: 58.14; 7.04; 6.73; 17.01.]

Following essentially the same procedure, and replacing ethyl 4-dimethylamino-2-phenylbutanoate with
ethyl 4-dimethylamino-2-(4-chlorophenyl)butanoate,
ethyl 4-dimethylamino-2-(2-methylphenyl)butanoate,
ethyl 4-dimethylamino-2-(4-methoxyphenyl)butanoate, and
ethyl 4-dimethylamino-2-(3-nitrophenyl)butanoate,
the following compounds can be prepared:
ethyl-2-[hydroxy(2-pyridyl)methyl]-4-dimethylamino-2-(4-chlorophenyl)butanoate,
ethyl 2-[hydroxy(2-pyridyl)methyl]-4-dimethylamino-2-(2-methylphenyl)butanoate,
ethyl 2-[hydroxy(2-pyridyl)methyl]-4-dimethylamino-2-(4-methoxyphenyl)butanoate, and
ethyl 2-[hydroxy(2-pyridyl)methyl]-4-dimethylamino-2-(3-nitrophenyl)butanoate, respectively.

EXAMPLES 6–22

In Examples 6–22, substitution of an equivalent quantity of another compound for benzaldehyde, and/or substitution of an equivalent quantity of another compound for N,N-dimethyl-4-dimethylamino-2-phenylbutanamide, in the procedure described in Example 1 resulted in the title compound of the Example as a mixture of diastereoisomers.

EXAMPLE 6

Preparation of
N,N-Dimethyl-2-[hydroxy(2-pyridyl)methyl]-4-dimethylamino-2-phenylbutanamide The title compound was produced by substitution of 2-pyridinecarboxaldehyde for benzaldehyde in Example 1. [Anal. Calc'd for C$_{20}$H$_{27}$N$_3$O$_2$: C, 70.35; H, 7.97; N, 12.31. Found: C, 69.83; H, 7.82; N, 12.36.]

EXAMPLE 7

Preparation of
N,N-Dimethyl-2-(hydroxycyclohexylmethyl)-4-dimethylamino-2-phenylbutanamide The title compound was produced by substitution of cyclohexanecarboxaldehyde for benzaldehyde in Example 1. [Anal. Calc'd for C$_{21}$H$_{34}$N$_2$O$_2$.HCl: C, 65.86; H, 9.21; N, 7.31; Cl, 9.26. Found: C, 65.76; H, 9.30; N, 7.24; Cl, 9.39.]

EXAMPLE 8

Preparation of
N,N-Dimethyl-2-(hydroxyphenylmethyl)-4-diisopropylamino-2-phenylbutanamide The title compound was produced by substitution of N,N-dimethyl-4-diisopropylamino-2-phenylbutanamide for N,N-dimethyl-4-dimethylamino-2-phenylbutanamide in Example 1. [Anal. Calc'd for C$_{25}$H$_{36}$N$_2$O$_2$.HCl: C, 69.34; H, 8.61; N, 6.47; Cl, 8.79. Found: C, 69.26; H, 8.46; N, 6.44; Cl, 8.47.]

EXAMPLE 9

Preparation of
N,N-Dimethyl-2-(hydroxyphenylmethyl)-4-piperidino-2-phenylbutanamide The title compound was produced by substitution of N,N-dimethyl-4-piperidino-2-phenylbutanamide for N,N-dimethyl 4-dimethylamino-2-phenylbutanamide in Example 1. [Anal. Calc'd for C$_{24}$H$_{32}$N$_2$O$_2$.HCl.½H$_2$O: C, 67.67; H, 8.04; N, 6.58; Cl, 8.32. Found: C, 67.98; H, 8.02; N, 6.68; Cl, 8.60.]

EXAMPLE 10

Preparation of
N,N-Dimethyl-2-(hydroxyphenylmethyl)-5-dimethylamino-2-phenylpentanamide The title compound was produced by substitution of N,N-dimethyl-5-dimethylamino-2-phenylpentanamide for N,N-dimethyl-4-dimethylamino-2-phenylbutanamide in Example 1. [Anal. Calc'd for C$_{22}$H$_{30}$N$_2$O$_2$.HCl.¾H$_2$O: C, 65.49; H, 7.87; N, 6.94; Cl 8.79. Found: C, 65.21; H, 8.25; N, 6.92; Cl, 9.20.]

EXAMPLE 11

Preparation of
N,N-Dimethyl-2-[hydroxy(2-chlorophenyl)methyl]-5-dimethylamino-2-phenylpentanamide The title compound was produced by substitution of N,N-dimethyl-5-dimethylamino-2-phenylpentanamide for N,N-dimethyl-4-dimethylamino-2-phenylbutanamide, as well as substitution of 2-chlorobenzaldehyde for benzaldehyde, in Example 1. [Anal. Cal'd for C$_{22}$H$_{29}$N$_2$O$_2$Cl.HCl: C, 62.12; H, 7.11; N, 6.59; Cl, 16.67. Found: C, 62.00; H, 7.12; N, 6.37; Cl, 16.46.]

EXAMPLE 12

Preparation of
N,N-Dimethyl-2-[hydroxy(3-chlorophenyl)methyl]-5-dimethylamino-2-phenylpentanamide The title compound was produced by substitution of N,N-dimethyl-5-dimethylamino-2-phenylpentanamide for N,N-dimethyl-4-dimethylamino-2-phenylbutanamide, as well as substitution of 3-chlorobenzaldehyde for benzaldehyde, in Example 1. [Anal. calc'd for C$_{22}$H$_{29}$N$_2$O$_2$Cl.HCl: C, 62.12; H, 7.11; N, 6.59; Cl, 16.67. Found: C, 61.88; H, 7.32; N, 7.32; Cl, 16.40.]

EXAMPLE 13

Preparation of
N,N-Dimethyl-2-[hydroxy(4-chlorophenyl)methyl]-5-dimethylamino-2-phenylpentanamide The title compound was produced by substitution of N,N-dimethyl-5-dimethylamino-2-phenylpentanamide for N,N-dimethyl-4-dimethylamino-2-phenylbutanamide, as well as substitution of 4-chlorobenzaldehyde for benzaldehyde, in Example 1. [Anal. Calc'd for C$_{22}$H$_{29}$N$_2$O$_2$Cl.HCl: C, 62.12; H, 7.11; N, 6.59; Cl, 16.67. Found: C, 62.26; H, 7.06; N, 6.66; Cl, 16.32.]

EXAMPLE 14

Preparation of
N,N-Dimethyl-2-[hydroxy(2,4-dichlorophenyl)methyl]-5-dimethylamino-2-phenylpentanamide The title compound was produced by substitution of N,N-dimethyl-5-dimethylamino-2-phenylpentanamide

EXAMPLE 15

Preparation of
N,N-Dimethyl-2-[hydroxy(2-bromophenyl)methyl]-5-dimethylamino-2-phenylpentanamide The title compound was produced by substitution of N,N-dimethyl-5-dimethylamino-2-phenylpentanamide for N,N-dimethyl-4-dimethylamino-2-phenylbutanamide, as well as substitution of 2-bromobenzaldehyde for benzaldehyde, in Example 1. [Anal. Calc'd for $C_{22}H_{29}N_2O_2Br\cdot HBr$: C, 51.38; H, 5.88; N, 5.45; Br, 31.07. Found: C, 51.04; H, 5.98; N, 5.36; Br, 30.84.]

EXAMPLE 16

Preparation of
N,N-Dimethyl-2-[hydroxy(4-methoxyphenyl)methyl]-5-dimethylamino-2-phenylpentanamide The title compound was produced by substitution of N,N-dimethyl-5-dimethylamino-2-phenylpentanamide for N,N-dimethyl-4-dimethylamino-2-phenylbutanamide, as well as substitution of p-anisaldehyde for benzaldehyde in Example 1. [Anal. Calc'd for $C_{23}H_{32}N_2O_3\cdot HCl$: C, 65.62; H, 7.90; N, 6.65; Cl, 8.42. Found: C, 65.58; H, 7.99; N, 6.62; Cl, 8.55.]

EXAMPLE 17

Preparation of
N,N-Dimethyl-2-[hydroxy(2-methylphenyl)methyl]-5-dimethyl-amino-2-phenylpentanamide The title compound was produced by substitution of N,N-dimethyl-5-dimethylamino-2-phenylpentanamide for N,N-dimethyl-4-dimethylamino-2-phenylbutanamide, as well as substitution of o-tolualdehyde for benzaldehyde, Example 1. [Anal. Calc'd for $C_{23}H_{32}N_2O_2\cdot HCl\cdot\frac{3}{4}H_2O$: C, 66.01; H, 8.31; N, 6.69; Cl, 8.47. Found: C, 66.24; H, 8.02; N, 6.68; Cl, 9.04.]

EXAMPLE 18

Preparation of
N,N-Dimethyl-2-[hydroxy(4-methylphenyl)methyl]-5-dimethylamino-2-phenylpentanamide The title compound was produced by substitution of N,N-dimethyl-5-dimethylamino-2-phenylpentanamide for N,N-dimethyl-4-dimethylamino-2-phenybutanamide, as well as substitution of p-tolualdehyde for benzaldehyde, Example 1. [Anal. Calc'd for $C_{23}H_{32}N_2O_2\cdot HCl$: C, 68.21; H, 8.21; N, 6.92; Cl, 8.75. Found: C, 68.32; H, 8.23; N, 6.94; Cl, 8.88.]

EXAMPLE 19

Preparation of
N,N-Dimethyl-2-[hydroxy(3-nitrophenyl)methyl]-5-dimethylamino-2-phenylpentanamide The title compound was produced by substitution of N,N-dimethyl-5-dimethylamino-2-phenylpentanamide for N,N-dimethyl-4-dimethylamino-2-phenylbutanamide, as well as substitution of 3-nitrobenzaldehyde for benzaldehyde, in Example 1. [Anal. Calc'd for $C_{22}H_{29}N_3O_4\cdot HCl$: C, 60.61; H, 6.94; N, 9.64; Cl, 8.13. Found: C, 60.16; H, 7.07; N, 9.50; Cl, 8.50.]

for N,N-dimethyl-4-dimethylamino-2-phenylbutanamide, as well as substitution of 2,4-dichlorobenzaldehyde for benzaldehyde, in Example 1. Anal. Calc'd for $C_{22}H_{28}N_2O_2Cl_2\cdot HCl$: C, 57.46; H, 6.36; N, 6.09; Cl, 23.13. Found: C, 57.61; H, 6.25; N, 6.08; Cl, 23.36.]

EXAMPLE 20

Preparation of
N,N-Dimethyl-2-(hydroxyphenylmethyl)-5-diisopropylamino-2-phenylpentanamide The title compound was produced by substitution of N,N-dimethyl-5-diisopropylamino-2-phenylpentanamide for N,N-dimethyl-4-dimethylamino-2-phenylbutanamide in Example 1. [Anal. Calc'd for $C_{26}H_{38}N_2O_2\cdot HCl$: C, 69.85; H, 8.79; N, 6.27; Cl, 7.93. Found: C, 69.83; H, 8.87; N, 6.10; Cl, 8.03.]

EXAMPLE 21

Preparation of
N,N-Dimethyl-2-(hydroxyphenylmethyl)-5-piperidino-2-phenylpentanamide The title compound was produced by substitution of N,N-dimethyl-5-piperidino-2-phenylpentanamide for N,N-dimethyl-4-dimethylamino-2-phenylbutanamide in Example 1. [Anal. Calc'd for $C_{25}H_{38}N_2O\cdot HCl\cdot\frac{3}{4}H_2O$: C, 69.42; H, 9.44; N, 6.48; Cl, 8.20. Found: C, 68.28; H, 8.36; N, 6.34; U, 8.40.]

EXAMPLE 22

Preparation of
N,N-Dimethyl-2-(hydroxyphenylmethyl)-4-dimethylamino-2-(2-pyridyl)-butanamide The title compound was produced by substitution of N,N-dimethyl-4-dimethylamino-2-(2-pyridyl)-butanamide for N,N-dimethyl-4-dimethylamino-2-phenylbutanamide in Example 1. [Anal. Calc'd for $C_{20}H_{27}N_3O_2$: Cl, 70.35; H, 7.97; N, 12.43. Found: C, 70.16; H, 8.22; N, 12.43.]

Following essentially the procedure of Example 1, and replacing N,N-dimethyl-4-dimethylamino-2-phenylbutanamide with N,N-dimethyl-4-dimethylamino-2-(4-chlorophenyl)-butanamide,
N,N-dimethyl-4-dimethylamino-2-(2-methylphenyl)-butanamide,
N,N-dimethyl-4-dimethylamino-2-(4-methoxyphenyl)-butanamide, and
N,N-dimethyl-4-dimethylamino-2-(3-nitrophenyl)-butanamide, the following compounds can be made:
N,N-dimethyl-2-(hydroxyphenylmethyl)-4-dimethylamino-2-(4-chlorophenyl)butanamide,
N,N-dimethyl-2-(hydroxyphenylmethyl)-4-dimethylamino-2-(2-methylphenyl)butanamide
N,N-dimethyl-2-(hydroxyphenylmethyl)-4-dimethylamino-2-(4-methoxyphenyl)butanamide, and
N,N-dimethyl-2-(hydroxyphenylmethyl)-4-dimethylamino-2-(3-nitrophenyl)butanamide, respectively.

Following essentially the procedure of Example 1 and replacing N,N-dimethyl-4-dimethylamino-2-phenylbutanamide with
N,N-dimethyl-4-cyclohexylamino-2-phenylbutanamide,
N,N-dimethyl-5-cyclohexylamino-2-phenylpentanamide,
N,N-dimethyl-4-cyclopropylamino-2-phenylbutanamide, and
N,N-dimethyl-5-cyclopropylamino-2-phenylpentanamide, the following compounds can be made:
N,N-dimethyl-2-(hydroxyphenylmethyl)-4-cyclohexylamino-2-phenylbutanamide, N,N-dimethyl-2-(hydroxyphenylmethyl)-5-cyclohex-
  ylamino-2-phenylpentanamide,
N,N-dimethyl-2-(hydroxyphenylmethyl)-4-cyclo-
  propylamino-2-phenylbutanamide, and
N,N-dimethyl-2-(hydroxyphenylmethyl)-5-cyclo-
  propylamino-2-phenylpentamide, respectively.

EXAMPLE 23

Preparation of
N-Methyl-2-(hydroxyphenylmethyl)-5-dimethylamino-
2-phenylpentanamide To N-methyl-5-dimethylamino-2-phenylpentanamide (5.0 g, 0.023 mol) dissolved in 50 ml THF was added 18.1 ml of a 2.5M solution of n-BuLi in n-hexane with ice-cooling under $N_2$. After stirring at 0° C. for 30 min, benzaldehyde (2.4 g, 0.023 mol) dissolved in 10 ml THF was added dropwise to the foregoing solution. The reaction mixture was stirred for 5 min at 0° C. and then poured into ice-cold HCl. The resulting solution was washed with $Et_2O$, basified by adding dilute NaOH while stirring in the cold, and extracted with $CHCl_3$. The $CHCl_3$ extract were combined, dried ($Na_2SO_4$), and evaporated Chromatography of the post-evaporation residue afforded the desired compound as a mixture of diastereoisomers as an oil. Dissolution in EtOH, acidification with HCl, followed by addition of $Et_2O$ gave the hydrochloride salt as a colorless solid. [Anal. Calc'd for $C_{21}H_{28}N_2O_2 \cdot HCl \cdot \frac{1}{4}EtOH$: C, 66.17; H, 7.93; N, 7.18; Cl, 9.08. Found: C, 65.82; H, 8.02; N, 7.04; Cl 10.27.]

EXAMPLE 24

Preparation of
2-(Hydroxyphenylmethyl)-4-dimethylamino-2-phenyl-
butanenitrile

Substitution of one equivalent quantity of benzaldehyde for 2-pyridinecarboxaldehyde in the procedure of Example 4 afforded the title compound as a mixture of diastereoisomers. [Anal. Calc'd for $C_{19}H_{22}N_2O$: C, 77.52; H, 7.53; N, 9.52. Found: C, 77.27; H, 7.45; N, 9.59.]

EXAMPLE 25

Preparation of
2-(Hydroxyphenylmethyl)-5-dimethylamino-2-phenyl-
pentanenitrile

Substitution of one equivalent quantity of 5-dimethylamino-2-phenylpentanenitrile for 4-dimethylamino-2-phenylbutanenitrile and one equivalent quantity of benzaldehyde for 2-pyridinecarboxaldehyde in the procedure of Example 4 afforded the title compound as a mixture of diastereoisomers. [Anal. Calc'd for $C_{20}H_{24}N_2O$: C, 77.89; H, 7.84; N, 9.08. Found: C, 76.58; H, 7.00; N, 8.94.]

EXAMPLE 26

Preparation of
2-[Hydroxy(2-pyridyl)methyl]-5-dimethylamino-2-
phenylpentanenitrile Substitution of one equivalent quantity of 5-dimethylamino-2-phenylpentanenitrile for 4-dimethylamino-2-phenylbutanenitrile in the procedure of Example 4 afforded the title compound as a mixture of diastereoisomers. [Anal. Calc'd for $C_{19}H_{23}N_3O$: C, 73.76; H, 7.49; N, 13.58. Found: C, 73.69; H, 7.55; N, 13.69.]

EXAMPLE 27

Preparation of Ethyl
2-(Hydroxyphenylmethyl)-4-dimethylamino-2-phenyl-
butanoate Substitution of one equivalent quantity of benzaldehyde for 2-pyridinecarboxaldehyde in the procedure in Example 5 afforded the individual diastereoisomers of the title compound: high $r_f$ diastereoisomer (mp 113°–115° C.); low $r_f$ diastereoisomer (mp 72°–74° C.).

EXAMPLE 28

Preparation of Ethyl
2-(Hydroxyphenylmethyl)-5-dimethylamino-2-phenyl-
pentanoate Substitution of one equivalent quantity of ethyl 5-dimethylamino-2-phenylpentanoate for 4-dimethylamino-2-phenylbutanoate and benzaldehyde for 2-pyridinecarboxaldehyde in the procedure in Example 5 afforded the individual diastereoisomers of the title compound: high $r_f$ diastereoisomer (mp 113°–115°), low diastereoisomer (mp 91°–93°).

EXAMPLE 29

Preparation of
N,N-Dimethyl-2-[hydroxy-(4-methoxyphenyl)methyl]-
4-dimethylamino-2-phenylbutanamide The title compound was produced by substitution of p-anisaldehyde for benzaldehyde in Example 1. The chromatography step led to the isolation of the pure diastereoisomers as free bases. Treatment of the free bases with EtOH/HCl afforded the solid HCl salts: (high $r_f$ diastereoisomer, mp 205°–207° C.; low $r_f$ diastereoisomer, mp 175°–176° C.).

EXAMPLE 30

Preparation of
N,N-Dimethyl-2-[(acetyloxy)phenylmethyl]-4-dime-
thylamino-2-phenylbutanamide, High melting point
diastereoisomer To 9.0 g (0.026 mol) of N,N-dimethyl-2-(hydroxyphenylmethyl)-4-dimethylamino-2-phenylbutanamide, high $r_f$ diastereoisomer, dissolved in 150 ml of dry pyridine, was added 7.4 g (0.071 mol) of acetic anhydride, and the clear solution was stirred at RT under $N_2$ for 40 hours. The solvent was then evaporated off at reduced pressure and the remaining oil partitioned between $CHCl_3$ and aq. $NaHCO_3$. The $CHCl_3$ extract was dried and evaporated to afford the product as a light yellow oil. Dissolution in ETOH and acidification with ETOH/HCl followed by addition of ether in the cold gave the hydrochloride salt of the title compound, as a colorless solid; yield 8.3 g (76.2%), mp 280° (dec.).

EXAMPLE 31

Preparation of
N,N-Dimethyl-2-[(acetyloxy)phenylmethyl]-4-dime-
thylamino-2-phenylbutanamide, Low melting point
diastereoisomer Substitution of one equivalent quantity of N,N-dimethyl-2-(hydroxyphenylmethyl)-4-dimethylamino-2-phenylbutanamide, low $r_f$ diastereoisomer, for N,N-dimethyl-2-(hydroxyphenylmethyl)-4-dimethylamino-2-phenylbutanamide, high $r_f$ diastereoisomer, in the procedure of Example 30 afforded the title compound as its hydrochloride salt. (mp 230°–232°).

EXAMPLE 32

Preparation of N,N-Dimethyl-2-[(acetyloxy)(4-methoxyphenyl)methyl]-4-dimethylamino-2-phenylbutanamide, High melting point diastereoisomer Substitution of one equivalent quantity of N,N-dimethyl-2-[hydroxy-(4-methoxyphenyl)methyl]-4-dimethylamino-2-phenylbutanamide, high $r_f$ diastereoisomer, for N,N-dimethyl-2-(hydroxyphenylmethyl)-4-dimethylamino-2-phenylbutanamide, high $r_f$ diastereoisomer, in the procedure of Example 30 afforded the title compound as its hydrochloride salt. (mp 248°–253°).

EXAMPLE 33

Preparation of N,N-Dimethyl-2-[(acetyloxy)(4-methoxyphenyl)methyl]-4-dimethylamino-2-phenylbutanamide, Low melting point diastereoisomer Substitution of one equivalent quantity of N,N-dimethyl-2-[hydroxy(4-methoxyphenyl)methyl]-4-dimethylamino-2-phenylbutanamide, low $r_f$ diastereoisomer, for N,N-dimethyl-2-(hydroxyphenylmethyl)-4-dimethylamino-2-phenylbutanamide, high $r_f$ diastereoisomer, in the procedure of Example 30 afforded the title compound as the hydrochlorid salt. (mp 220°–223°).

EXAMPLE 34

Preparation of N,N-Dimethyl-2-[hydroxy(3-pyridyl)methyl]-4-dimethylamino-2-phenylbutanamide The title compound was produced by substitution of 3-pyridinecarboxaldehyde for benzaldehyde in Example 1. [Anal. Calc'd for $C_{20}H_{27}N_3O_2$: C, 70.35; H, 7.97; N, 12.31. Found: C, 70.23; H, 8.03; N, 2.25]

EXAMPLE 35

Preparation of N,N-Dimethyl-2-[hydroxy(4-pyridyl)methyl]-4-dimethylamino-2-phenylbutanamide The title compound was produced by substitution of 4-pyridinecarboxaldehyde for benzaldehyde in Example 1. [Anal Calc'd for $C_{20}H_{27}N_3O_2.2HCl.\frac{1}{2}H_2O$.C, 56.74; H, 7.14; N, 9.92; Cl, 16.75. Found: C, 55.84; H, 6.94; N, 9.76; Cl, 17.57].

EXAMPLE 36

Preparation of N,N-Dimethyl-3-hydroxy-2-dimethylaminoethyl-2-phenylpentanamide

The title compound was produced by substitution of propionaldehyde for benzaldehyde in Example 1. [Anal. Calc'd $C_{17}H_{28}N_2O_2.HCl$: C, 62.09; H, 8.89; N, 8.52; Cl, 10.78. Found C, 61.53; H, 8.97; N, 8.60; Cl, 10.95].

What is claimed is:

1. A method of treating angina comprising the administration, to a mammal in need of such treatment, of an effective amount of a compound of the formula

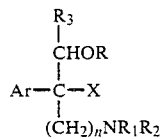

wherein
R is hydrogen or lower alkanoyl;
$R_1$ and $R_2$ are independently hydrogen, lower alkyl, or lower cycloalkyl, or $R_1$ and $R_2$ together with their adjacent nitrogen atom form a heterocyclic ring containing 4 to 6 carbon atoms;
$R_3$ is phenyl, substituted phenyl, 2-pyridyl, 3-pyridyl, 4-pyridyl, lower alkyl or lower cycloalkyl;
Ar is phenyl, substituted phenyl, or 2-pyridyl;
X is $CO_2R_4$ or $CONR_5R_6$;
$R_4$ is hydrogen or lower alkyl;
$R_5$ and $R_6$ are independently hydrogen or lower alkyl, or
$R_5$ and $R_6$ together with their adjacent nitrogen atom form a heterocyclic ring containing 4 to 6 atoms; and
n is 2 or 3, including all enantiomers thereof and mixtures of enantiomers thereof.

2. A method of treating an arrhythmic heart condition comprising the administration, to a mammal in need of such treatment, of an effective amount of a compound of the formula

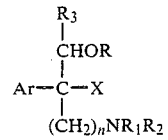

wherein:
R is hydrogen or lower alkanoyl;
$R_1$ and $R_2$ are independently hydrogen, lower alkyl, or lower cycloalkyl, or $R_1$ and $R_2$ together with their adjacent nitrogen atoms form a heterocyclic ring containing 4 to 6 carbon atoms;
$R_3$ is phenyl, substituted phenyl, 2-pyridyl, lower alkyl or lower cycloalkyl;
Ar is phenyl, substituted phenyl, or 2-pyridyl;
X is $CO_2R_4$ or $CONR_5R_6$;
$R_4$ is hydrogen or lower alkyl;
$R_5$ and $R_6$ are independently hydrogen or lower alkyl, or
$R_5$ and $R_6$ together with their adjacent nitrogen atom form a heterocyclic ring containing 4 to 6 atoms; and
n is 2 or 3, including all enantiomers thereof and mixtures of enantiomers thereof, provided that:
(1) $R_3$ is not 2-pyridyl in a compound in which X is $CONHCH_3$, R is H, Ar is phenyl, and n is 2; and
(2) $R_3$ is not phenyl substituted with lower alkoxy in a compound in which X is $CON(CH_3)_2$, R is H, Ar is phenyl and n is 3.

3. The method as defined in claim 2 wherein $R_1$ and $R_2$ are both $CH_3$, $R_3$ is phenyl, R is hydrogen, Ar is phenyl, X is $CON(CH_3)_2$ and n is 2.

4. The method as defined in claim 2 wherein $R_1$ and $R_2$ are both $CH_3$, $R_3$ is phenyl, R is hydrogen, Ar is phenyl, X is $CON(CH_3)_2$ and n is 3.

5. The method as defined in claim 2 wherein $R_1$ and $R_2$ are both $CH_3$, $R_3$ is 2-pyridyl, R is hydrogen, Ar is phenyl, X is $CO_2C_2H_5$ and n is 2.

6. The method as defined in claim 2 wherein $R_1$ and $R_2$ are both $CH_3$, $R_3$ is phenyl, R is hydrogen, Ar is phenyl, X is $CO_2C_2H_5$ and n is 3.

7. The method as defined in claim 2 wherein $R_1$ and $R_2$ are both isopropyl, $R_3$ is phenyl, R is hydrogen, Ar is phenyl, X is $CON(CH_3)_2$ and n is 2.

8. The method as defined in claim 2 wherein $R_1$ and $R_2$ are methyl, $R_3$ is 4-methoxyphenyl, R is hydrogen, Ar is phenyl, X is $CON(CH_3)_2$ and n is 2.

9. The method of claim 2 wherein R is acetyl, $R_1$ and $R_2$ are methyl, Ar is phenyl, $R_3$ is phenyl, X is $CON(CH_3)_2$ and n is 2.

10. The method of claim 2 wherein R is acetyl, $R_1$ and $R_2$ are methyl, Ar is phenyl, $R_3$ is 4-methoxyphenyl, X is $CON(CH_3)_2$ and n is 2.

11. The method of claim 2 wherein R is hydrogen, $R_1$ and $R_2$ together with their adjacent nitrogen atom form piperidino, Ar is phenyl, $R_3$ is phenyl, X is $CON(CH_3)_2$ and n is 2.

12. The method of claim 2 wherein R is hydrogen, $R_1$ and $R_2$ are isopropyl, Ar is phenyl, $R_3$ is phenyl, X is $CON(CH_3)_2$ and n is 3.

13. The method of claim 2 wherein R is hydrogen, $R_1$ and $R_2$ together with their adjacent nitrogen atom form piperidino, Ar is phenyl, $R_3$ is phenyl, X is $CON(CH_3)_2$ and n is 3.

* * * * *